(12) United States Patent
Zapata

(10) Patent No.: US 6,409,734 B1
(45) Date of Patent: Jun. 25, 2002

(54) AMNIOTOMY GLOVE

(76) Inventor: Helio Zapata, 4142 W. Cleveland, Skokie, IL (US) 60076

( * ) Notice: Subject to any disclaimer, the term of this patent is extended or adjusted under 35 U.S.C. 154(b) by 0 days.

(21) Appl. No.: 09/349,798

(22) Filed: Jul. 9, 1999

(51) Int. Cl.[7] ............................................... A61B 17/42
(52) U.S. Cl. ..................... 606/125; 606/119; 2/161.7
(58) Field of Search ................................ 606/119, 125; 2/161.7, 160

(56) References Cited

U.S. PATENT DOCUMENTS

| | | | | | |
|---|---|---|---|---|---|
| 2,084,692 A | * | 6/1937 | Little | ........................ | 606/125 |
| 2,847,012 A | * | 8/1958 | Eastman | ................... | 606/125 |
| 3,587,591 A | * | 6/1971 | Satterwhite | ................ | 606/125 |
| 3,687,139 A | * | 8/1972 | Poirier | ........................ | 606/125 |
| 3,735,760 A | * | 5/1973 | Vreeland, Jr. | .............. | 606/212 |
| 3,749,099 A | * | 7/1973 | Cotey | ......................... | 606/125 |
| 4,198,985 A | * | 4/1980 | Abel | ........................... | 606/125 |

* cited by examiner

*Primary Examiner*—Nicholas D. Lucchesi
*Assistant Examiner*—Michael B. Priddy
(74) *Attorney, Agent, or Firm*—Sidney N. Fox

(57) ABSTRACT

An amniotomy glove incorporating a puncturing hook in the shape of a falcon's beak mounted on a structural base which is bonded to the inner surface of a latex physician's glove at a location spaced slightly from the tip of middle finger stall of said glove. The hook extends through wall of the middle finger stall and is bonded to the latex wall of said middle finger stall.

6 Claims, 3 Drawing Sheets

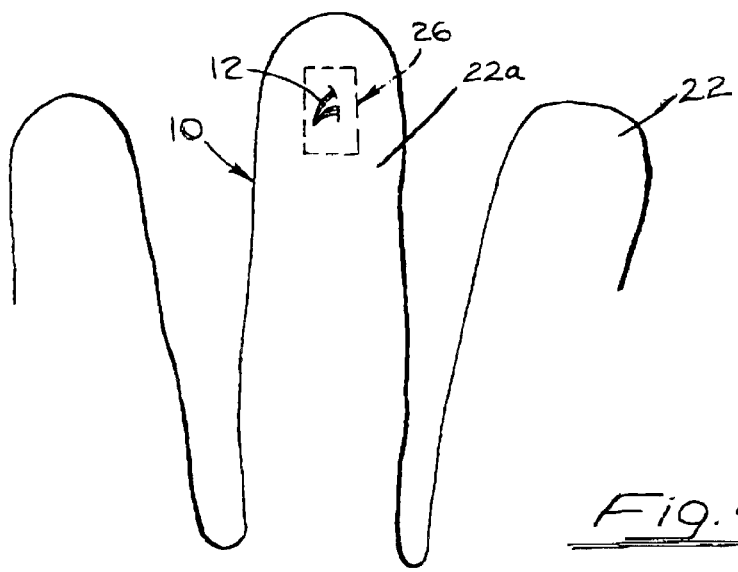
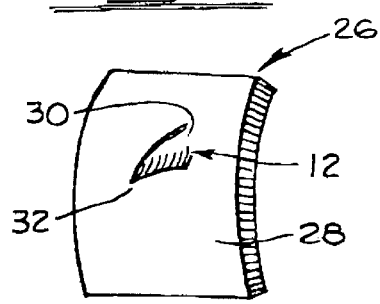
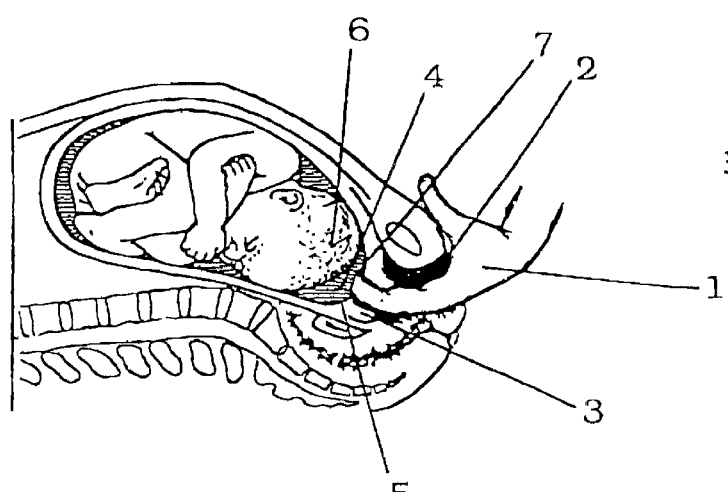

AMNIOTOMY GLOVE

FIELD OF THE INVENTION

This invention relates generally in the field of Medical Obstetrics where practitioners perform amniotomy procedures in which the amniotic membrane is ruptured artificially to make the process of labor more effective, and more particularly provides an instrument for performing the amniotomy procedures which can be worn by the physician and carries means for effectively rupturing the amnotic membrane overcoming problems encountered in effecting the amniotomy procedure.

BACKGROUND OF THE INVENTION

Amniotomy, the artificial rupturing of the fetal membrane, is a routine practice of laboring patients. Amniotomy is also performed, when ever possible, as an integral part of the care of laboring patients with a plastic stick 10½ inches long, with a small plastic hook at its narrower end. If seen under a magnifying glass, this small hook looks like a small, inverted falcon's beak. In order to perform an amniotomy with such a plastic stick, the cervix should be in an advanced state of effacement and should also be dilated. When the cervix, a hollow tube of fibrous tissue (whose axis is normally at an angle from that of the vagina), is neither effaced nor dilated, an instrument, such as a plastic stick carrying a hook would likely be useless since the straight, inflexible plastic stick cannot have access to an uneffaced cervix because of the curvature needed to overcome the angle between the intersecting axis of the vagina and the cervix.

The inability to perform an amniotomy in these extremely common circumstances, when the head is already engaged, becomes a frequent cause of frustration. The physician is faced with the alternative of waiting several hours for the cervix to open and efface before the plastic stick the plastic stick can be used to break the amnion. Often the desired dilation and effacement never takes place in spite of many hours of Prostaglandings or labor contractions. The process of labor has a statistically higher chance of success with amniotomy than without it. Not infrequently, a Cesarean sections is done for a dead fetus because all conventional means to deliver vaginally failed and in most of those cases, an amniotomy could not be done because of an uneffaced cervix. Another problem with using the plastic stick is its unpleasant and almost frightening appearance, causing apprehension in the patient when she sees the physician approaching her with a sizable stick to be inserted deep into her vagina.

BRIEF DESCRIPTION OF THE VIEWS OF THE DRAWING

FIG. 3, is an enlarged face view of certain amniotomy glove of the invention, the middle finger stall being shown as having the puncturing hook incorporated thereon;

FIG. 4, is a perspective view of the structural support base for the puncturing hook, the hook being shown incorporated therewith, and, FIG. 5, is a sectional view of the expectant mother's anatomy showing use of the amniotomy glove of the invention. FIG. 5 illustrates the terms identified in the forthcoming description of the process of amniotomy, namely, reference character 1 refers to the hand of the physician effecting an amniotomy, reference character 2 refers to the vaginal opening; reference character 3 refers to the cervix; reference character 4 refers to the amniotic fluid within the amnion; reference character 5 refers to the amnion; reference number 6 refers to the fetal head; and reference character 7 refers to the puncturing plastic hook attached to the middle finger stall of amniotomy glove.

The file of this patent contains at least one drawing executed in color. Copies of this patent with color drawing (s) will be provided by the Patent and Trademark Office upon request and payment of the necessary fee.

SUMMARY OF THE INVENTION

The amniotomy glove of the invention is an ordinary Latex physician's glove having finger and thumb stalls (a stall is defined as a protective sheath for a finger) and has a small plastic hook at the tip (or end) of the middle finger stall intimately bonded to the Latex material of the glove at a location spaced a slight distance from the end of the middle finger stall. The hook is bonded to a small supporting base underneath the Latex surface which is bonded to the interior surface of the middle finger stall, the puncturing hook having a downward curved body with a sharply pointed portion similar to a falcon's beak. The puncturing hook protrudes through the middle finger stall and extends longitudinally along the middle finger stall and is fixed thereon.

DETAILED DESCRIPTION OF THE PREFERRED EMBODIMENTS OF THE INVENTION

Figure 1:
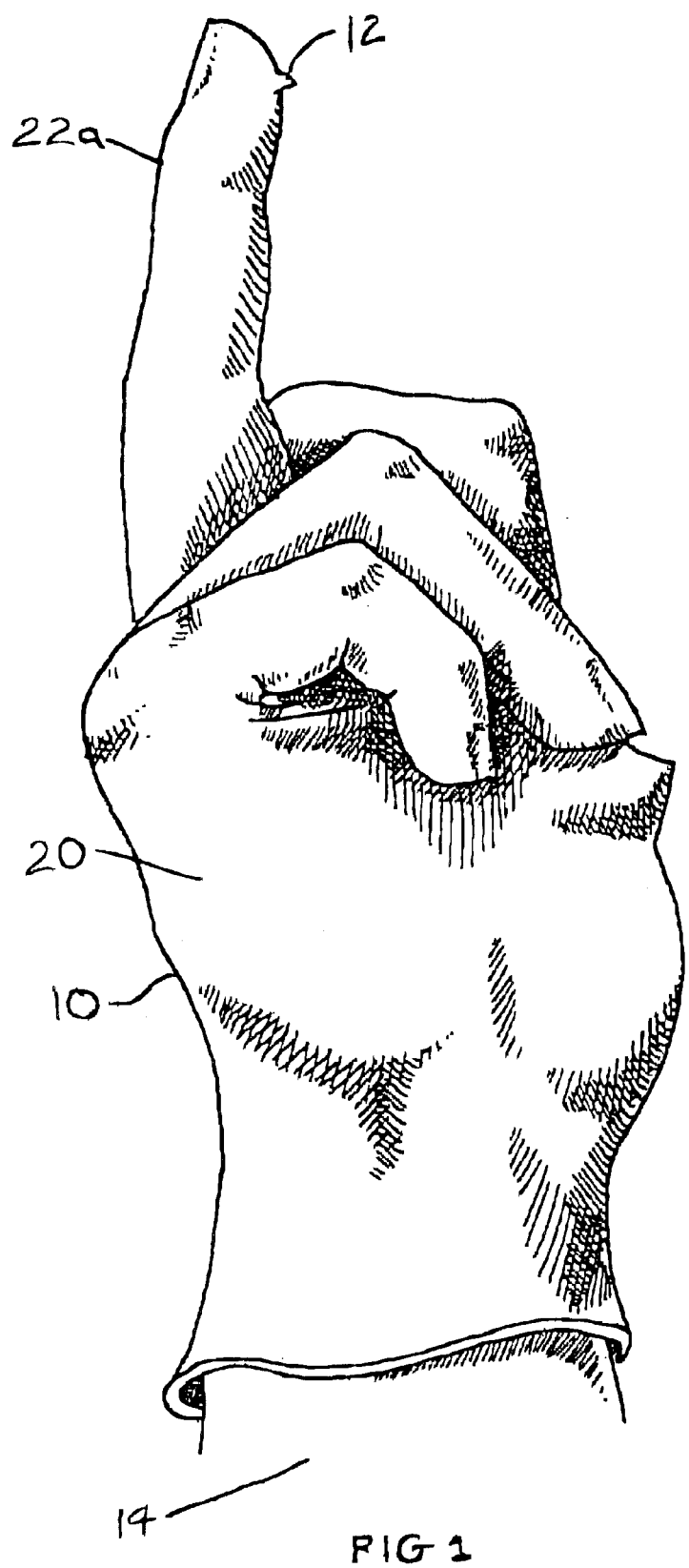
FIG. 1, is a perspective view of the amniotomy glove of the invention shown being viewed worn on a physician's hand, the puncturing hook being incorporated on the middle finger stall of the glove.
Figure 2:
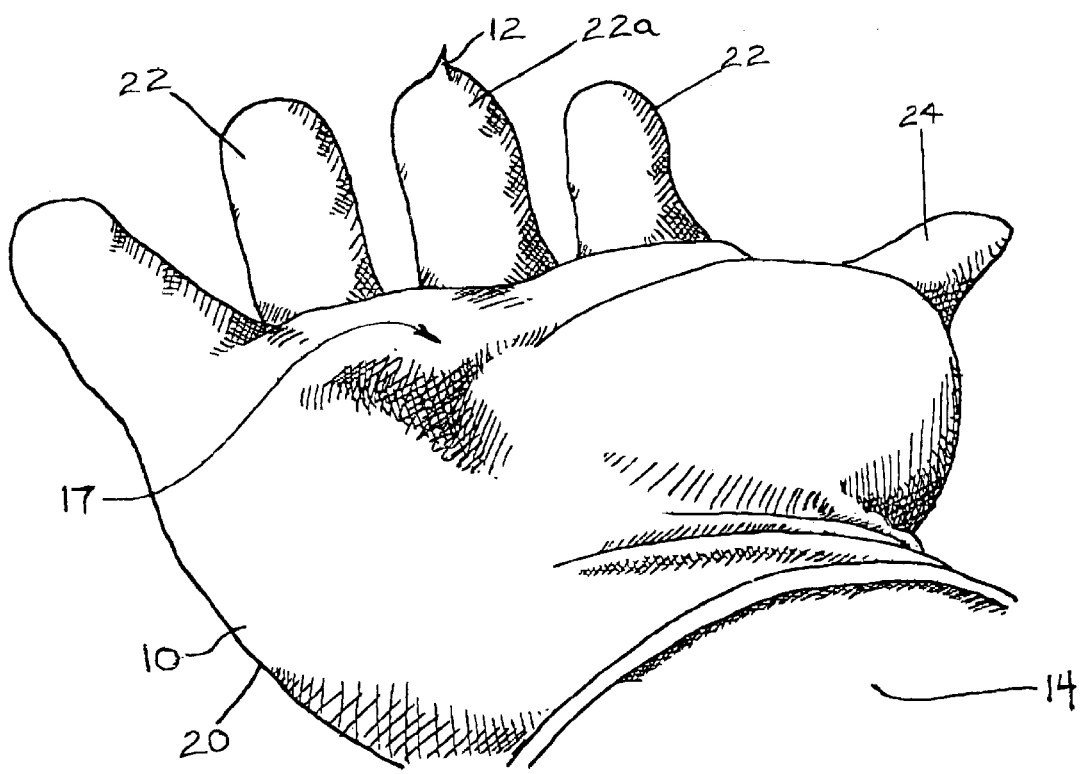
FIG. 2, is a perspective view of the amniotomy glove of the invention and being viewed From a different angle as shown in FIG. 1.

Attention now is directed to FIGS. 1 and 2 of the drawing wherein the amniotomy glove 10 as a whole is shown fitted on the hand of the user. The glove 10 carries a puncturing hook 12. The hand of the user is covered by the glove 10 with the wrist 14 being illustrated. The glove 10 is a standard physician's glove formed of single ply, elastic, yieldable, stretchable, resilient and flexible Latex material. The glove 10 has a main body 20 capable of being fitted on the hand 14 of the user and has finger and thumb stalls (a stall being defined as a protective sheath for the finger of the glove). The glove 10 has a main body 20 capable of being fitted over the hand 14 of the user and a middle finger stall 22a. A hook member 12 having the shape of a falcon's beak is spaced a slight distance from the extreme tip of the middle finger stall 22a and extends through the material of the middle finger stall. A preferred embodiment of the amniotomy glove of the invention is provided with a hook 12 measuring 2 mm. and has a round diameter at its base of 2 mm. The hook 12 has a downward curved body and a support base 28 which is relatively less flexible than the Latex material of the glove and is capable of being bond intimately to the upper surface of the support base 28 which is bonded to the inner surface of the middle finger stall, 22a. Only the hook 12 protrudes through the Latex material of the glove 10 and remains exterior of the glove 10. The hook measures 2 mm. and has a round diameter (at its base) of 2 mm.

A preferred embodiment of the support base 28 has a physical size and proportions as follows, length 15 mm., width 8 mm. and a thickness of 1 mm. As viewed in FIG. 4, body of the hook 12 is generally tapered from a relatively broad base and terminates in a relatively sharp puncturing point 32 as shown.

As illustrated in FIGS. 1 and 2, the tip of the middle finger stall 22a, has a curved shape, the shape of the tip of middle singer stall is determined by the structural base 28 to which it is bonded located inside the finger stall 22a, the shape being a result from being the closed end of the tubular finger stall 22a. The entire glove is impervious and without openings except for the entrance opening of the glove.

The structural support base is inside the linger stall 22a and secured thereto throughout the area of said base 28. The puncturing hook 12 is extended through the wall of the middle finger stall 22a as indicated by reference character 28. It is located so that it is positioned outwardly. The middle finger 22a is close enough to the extreme outer end of the middle finger stall 22a for simplification of the maneuvering of the glove. The point 32 of the puncturing hook extends from the hand of the user in the direction of the front or side portion of the hand although located at the extreme outer end. The point 32 of the puncturing hook is very small compared with the hand, or any of the fingers or portions thereof. When the hand is about to be used, the middle finger as well as the other fingers are flexed, making a fist (as shown in FIGS. 1 and 2 ) so that the hook 12 is not visible to the patient. Thus there is no fear developed in the patient as would likely occur where an external instrument or device is used. Further, since the hook 12 is extremely small, it does not interfere with manipulation of the finger nor cause any harm to surrounding tissue.

In view of the flexibility of the amniotomy glove of the invention, with its hook adjacent the tip of its middle finger, it can be manipulated in the most delicate fashion preventing unnecessary scratching to the fetal scalp. Considering the present equipment and methods used in current obstetrical medical practice, the physician having the benefit of using the amniotomy glove of the invention, will be able to perform an amniotomy in the very early stages of labor and even before labor starts, as long as there is an engaged fetal head. An early use of the amniotomy glove of the invention, may reduce the incidence of Cesarean sections significantly.

In summary, the amniotomy glove of the invention enables the physician, regardless of the cervical effacement, to insert the gloved middle finger into the cervix and reach the amnion so as to complete the amniotomy. The only limitation to the amniotomy glove as described herein would be a closed cervix or one that cannot be reached at all. The amniotomy glove as described makes possible amniotomy in the early stages of labor, even before labor starts. Using the amniotomy glove in an advanced cervical dilation enables the physician to conveniently rotate his middle finger to any position on the bulging bag of amniotic water that needs to be broken a log easier than with such instrument as an elongate plastic stick having a hook, which instrument must be held in the left hand 10½ inches away from the site of the intended rupture. For example, the physician may choose to rupture the amnion sac at the must further anterior as possible, even underneath the anterior lip of the cervix, to prevent a sudden gush of amniotic fluid and allow a gradual descent of the presenting part, a tactic that could not be accomplished with an inflexible, rigid plastic stick commonly used.

What I claim as my invention are:

1. An amniotomy glove formed of flexible elastic latex material and capable of fitting on the hand of the users said glove having thumb and finger stalls including a middle finger stall having an interior wall and a tip and capable of receiving the middle finger of the user, a structural base element having a puncturing hook portion bonded thereto, said structural base element being bonded to the interior wall of said middle finger stall at a location adjacent but spaced slightly from the tip of said middle finger stall with said puncturing hook portion extending through the interior wall of said middle finger enabling said puncturing hook portion to pierce the amniotic membrane for effecting the rupture thereof.

2. The amniotomy glove according to claim 1 wherein said glove has a palm side and said structural base element is in the form of a generally flat piece of material bonded to the inner surface of said middle finger stall that is on the palm side of said glove and located adjacent the tip of said middle finger stall.

3. The amniotomy glove according to claim 1 in which the tip of said middle finger stall is of curved configuration and said puncturing hook extends outward of the wall thereof.

4. The amniotomy glove according to claim 1 in which said puncturing hook portion extends outward at a location spaced from the tip of said middle finger stall.

5. The amniotomy glove according to claim 1 in which said puncturing hook portion has the configuration of an inverted falcon's beak.

6. The amniotomy glove according to claim 1 in which said hook portion extends outward and in a direction along the tip of middle finger stall and with the point thereof directed toward the palm of the hand of the user.

\* \* \* \* \*